United States Patent [19]

Kobzina

[11] 4,456,471
[45] Jun. 26, 1984

[54] HERBICIDAL N-HALOACETYL-2-METHYL-6-SUBSTITUTED METHOXYMETHYLANILINES

[75] Inventor: John W. Kobzina, Walnut Creek, Calif.

[73] Assignee: Chevron Research Company, San Francisco, Calif.

[21] Appl. No.: 402,396

[22] Filed: Jul. 27, 1982

Related U.S. Application Data

[60] Continuation-in-part of Ser. No. 172,788, Jul. 28, 1980, Pat. No. 4,348,222, which is a division of Ser. No. 53,877, Jul. 2, 1979, Pat. No. 4,244,730.

[51] Int. Cl.³ .................... A01N 37/22; C07C 103/38
[52] U.S. Cl. ........................................ 71/118; 564/214
[58] Field of Search .......................... 71/118; 564/214

[56]   References Cited
       U.S. PATENT DOCUMENTS

| | | | |
|---|---|---|---|
| 3,403,994 | 10/1968 | Olin | 71/118 |
| 3,404,976 | 10/1968 | Olin | 71/118 |
| 3,475,157 | 10/1969 | Olin | 71/118 |
| 4,146,387 | 3/1979 | Thiele | 71/118 |
| 4,224,050 | 9/1980 | Colle et al. | 71/98 |
| 4,261,733 | 4/1981 | Chupp | 71/118 |

FOREIGN PATENT DOCUMENTS 882415 3/1980 Belgium .
1392584 4/1975 United Kingdom .

*Primary Examiner*—Paul M. Coughlan, Jr.
*Attorney, Agent, or Firm*—S. R. LaPaglia; T. G. De Jonghe; L. S. Squires

[57] ABSTRACT

Compounds of the formula

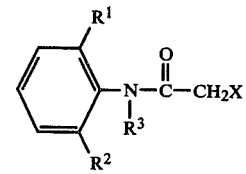

wherein $R^1$ is alkyl or alkoxy; $R^2$ is alkenyl having 2 to 10 carbon atoms, substituted alkyl of 1 to 10 carbon atoms or substituted alkenyl of 1 to 10 carbon atoms substituted with 1 or 2 hydroxy groups or 1 or 2 alkoxy groups of 1 to 4 carbon atoms or 1 or 2 alkenyloxy groups of 2 to 4 carbon atoms; acyl, and ketal group of the formula

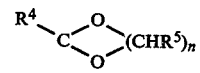

wherein $n=2$, 3 or 4, $R^4$ is alkyl and $R^5$ is hydrogen or alkyl, an oxime of the formula

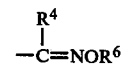

wherein $R^6$ is hydrogen or alkyl; $R^3$ is hydrogen or alkyl; X is halo have herbicidal activity.

18 Claims, No Drawings

HERBICIDAL N-HALOACETYL-2-METHYL-6-SUBSTITUTED METHOXYMETHYLANILINES

CROSS-REFERENCE TO RELATED APPLICATIONS

This application is a continuation-in-part of copending application Ser. No. 172,788, filed July 28, 1980, now U.S. Pat. No. 4,348,222 which is a division of application Ser. No. 53,877, filed July 2, 1979, now U.S. Pat. No. 4,244,730. The disclosures of all of which applications are hereby incorporated by reference in their entirety.

BACKGROUND OF THE INVENTION

U.S. Pat. No. 4,141,989 discloses 3-(N-chloroacetyl-N-2,6-dialklyphenylamino)-gamma-butyrolactones as fungicides.

U.S. Pat. No. 4,055,410 discloses substituted bromo and chloroacetamides as herbicides.

SUMMARY OF THE INVENTION

This invention relates to novel N-haloacetyl-2-alkyl 6-acylaniline compounds and derivatives thereof, methods of their use as herbicides and herbicidal compositions thereof. It has now been found that the placement of certain acyl, ketal, oxime, hydroxyalkyl and alkoxyalkyl substituents on the 6-position of N-haloacetyl-2-alkyl anilines results in compounds having herbicidal activity. The compounds of the invention are especially effective for pre-emergent treatment of grassy weeds.

DESCRIPTION OF THE INVENTION

The compounds of the invention are represented by the formula:

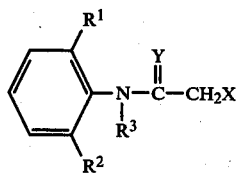
(I)

wherein $R^1$ is alkyl of 1 to 4 carbon atoms; or alkoxy of 1 to 4 carbon atoms; $R^2$ is substituted alkyl of 1 to 6 carbon atoms or substituted alkenyl of 1 to 6 carbon atoms substituted with 1 or 2 hydroxy groups or 1 or 2 alkoxy groups of 1 to 3 carbon atoms; acyl of 2 to 4 carbon atoms; a group of the formula

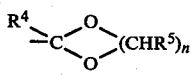

wherein n=2, 3 or 4; $R^4$ is alkyl of 1 to 3 carbon atoms and $R^5$ is hydrogen or alkyl of 1 to 3 carbon atoms; a group of the formula:

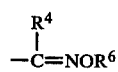

wherein
$R^4$ is defined above and $R^6$ is hydrogen or alkyl of 1 to 3 carbon atoms;

$R^3$ is hydrogen or alkyl of 1 to 4 carbon atoms;
X is halogen; and
Y is oxygen or sulfur.

Representative $R^1$ groups are methyl, ethyl, n-propyl, i-propyl, methoxy, ethoxy and i-propoxy. Preferably $R^1$ is methyl.

Representative substituted alkyl and acyl $R^2$ groups are 1-hydroxyethyl, 1,2-bis-methoxyethyl, 1-methyl-1-methoxyethyl, 1-ethyl-1-methoxypropyl, 1-propyl-1-methoxybutyl, 1-butyl-1-methoxypentyl, 1-propyl-1-propoxybutyl, 1-butyl-1-propoxypentyl, 1-methyl-1-methoxybutyl, 1-ethyl-1-prop-2-enyloxy, acetyl and propionyl.

Representative oxime $R^2$ groups are

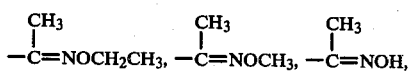

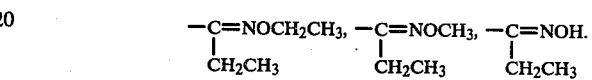

Representative $R^3$ groups are hydrogen, methyl, ethyl, i-propyl, n-propyl, n-butyl, i-butyl. Preferably $R^3$ is hydrogen or methyl. $R^2$ is preferably

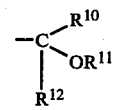

wherein $R^{10}$, $R^{11}$, and $R^{12}$ are independently selected from the group of lower alkyl having 1–4 carbon atoms.

Representative X groups are chloro, bromo, fluoro, iodo. Preferably X is chloro. Preferably Y is oxygen.

It has now further been found that, although the compounds of Formula I hereinabove have good pre-emergence activity against grasses, that within this genus the compounds of the sub-genus indicated by Formula (I') hereinbelow have surprisingly superior pre-emergence activity against grasses.

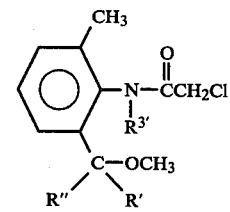
(I')

wherein R' and R" are independent of the other methyl or ethyl and $R^{3'}$ is hydrogen or methyl.

The compounds of Formula I' are effective at very low dosages and exhibit safety with respect to soybean, cotton, and peanut crops. The compounds of Formula (I') wherein $R^3$ is methyl, are slightly less active than the compounds wherein $R^3$ is hydrogen compounds but also have a slightly higher safety factor with respect to the aforementioned crops. In terms of pre-emergence activity against grasses per unit cost best results are obtained using the compound of Formula I' wherein $R^{3'}$ is hydrogen or methyl and R' and R" are each methyl.

The compounds of the invention can be made according to the following schemes.

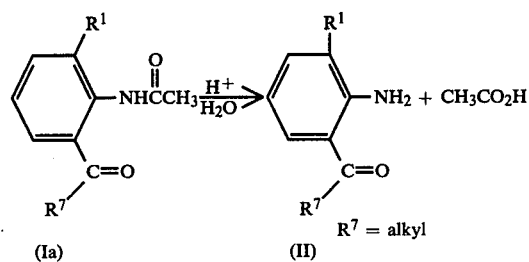 (1)
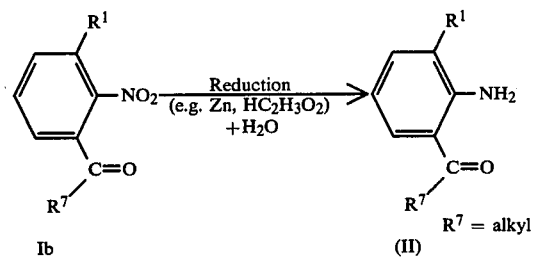 (1a)
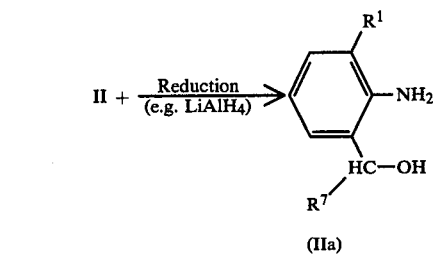 (1b)
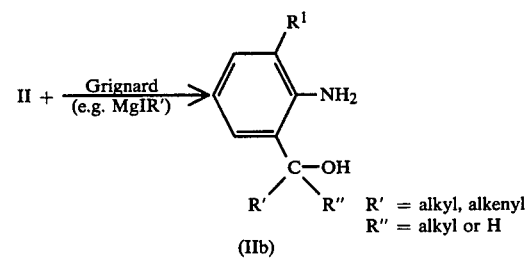 (2)
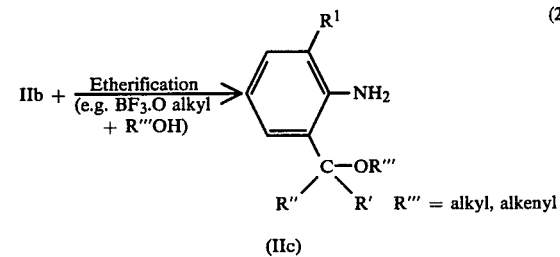 (2a)
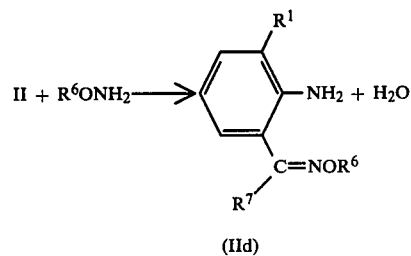 (2b)
-continued
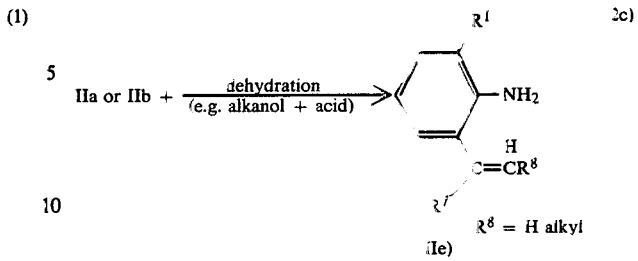 (2c)
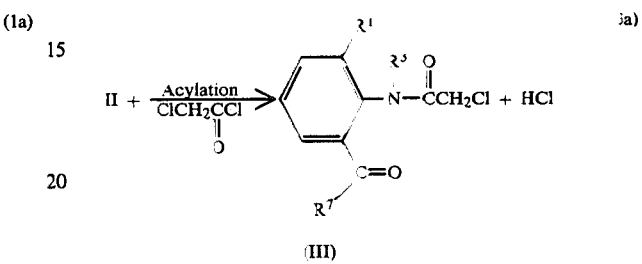 (3a)
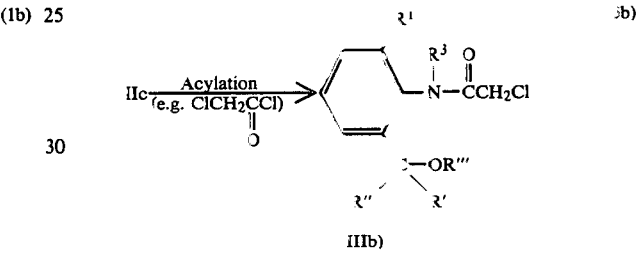 (3b)
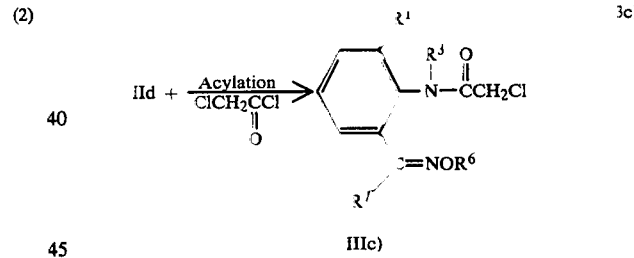 (3c)
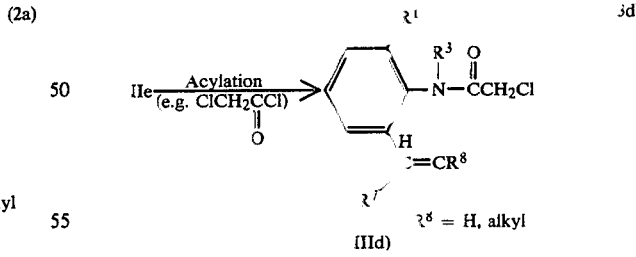 (3d)
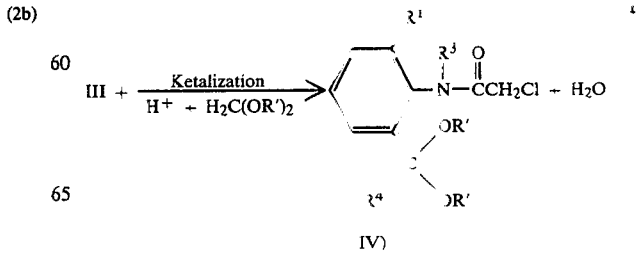 (4)

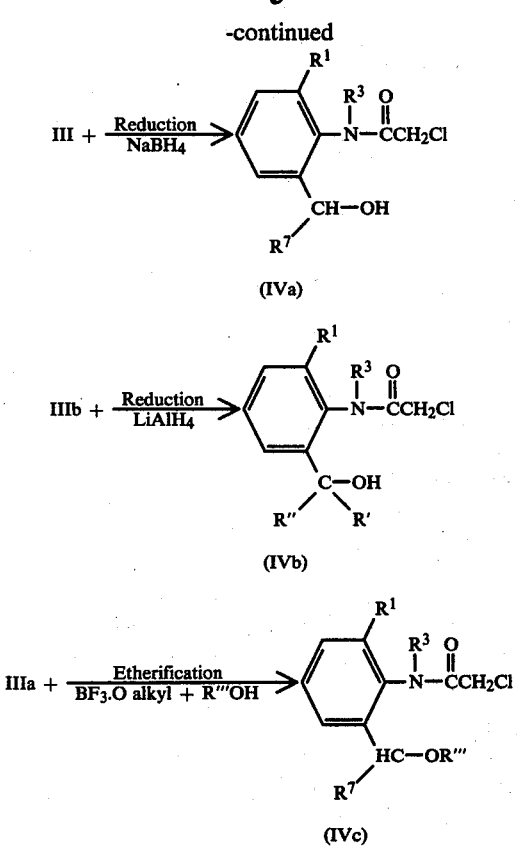

The above reactions are conventional reactions: deacetylation (1); reduction (1a, 1b, 4a and 4b) Grignard (2); etherification (2a and 4c), acetylation (3a, 3b, 3c and 3d), dehydration (2c) and ketalization (4) and can be performed by known procedures. The general preparation of compounds of the type represented by Formula IIb is also described in U.S. Pat. No. 3,917,592. Reaction (2b) is generally conducted by reacting substantially equimolar amounts of the carbonyl compound (II) and the alkoxyamine in the liquid phase in an inert diluent at a temperature of 0° to 100° C. Generally, the alkoxyamine is generated in situ from the corresponding alkoxyamino hydrochloride or methoxyamine hydrochloride, and a base, e.g., an inorganic alkali metal carbonate such as potassium carbonate or a trialkylamine such as triethylamine. Also, although for convenience, chloroacetyl chloride has been shown as the acylating agent, because it is preferred, other haloacetyl halides (e.g. bromoacetyl bromide) could also be used.

The acetylation (i.e. haloacetylation) is typically conducted as the last step in the preparation of the present compounds. As above noted the acetylation is a conventional reaction and is typically conducted at temperatures in the range of about from 20° to 150° C., preferably 10° to 50° C., for about from 10 minutes to 72 hours, preferably 3 to 24 hours using about from 0.5 to 10 moles, preferably 1 to 3 moles of the acylating agent per mole of anilino reactant. Typically, the acylation is conducted in a suitable inert organic solvent such as, for example, alkyl ethers, (e.g. ethyl ether) aromatics (e.g., benzene, toluene), halogenated alkanes (methylene chloride); alkyl esters (e.g., ethyl acetate), liquid alkanes (e.g., hexane), and the like.

Also, although for simplicity the anilino reactant has been shown as unsubstituted at the N position in the reaction equations, the N-$R^3$ substituted compounds can be prepared in the same manner by using the appropriate $R^3$ substituted starting material.

Generally, the above reactions are conducted as liquid phase reactions and hence pressure is generally not material except so far as it affects the temperature of reactions conducted at reflux. For example, the reactions can be conducted at pressures in the range of from 200 to 5000 mm Hg and conveniently are conducted at atmospheric or ambient pressure.

The compounds of the present invention are, in general, herbicidal in both pre- and post-emergent applications, but are particularly effective in pre-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broadleaved weeds. Some may be selective with respect to the type of application and/or type of weed. The compounds of the invention are particularly effective as pre-emergent herbicides against weed grasses.

The compounds, when applied to growing plants above the ground in such an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees.

The compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert an herbicidal or growth regulating effect. Usually from about 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agent. Natural clays, either absorptive, such as attapulgite, or relatively nonabsorptive, such as china clays, diatomaceous earth, synthetic fine silica, calcium silicate and other inert solid carriers of the kind conventionally employed in powdered herbicidal compositions can be used. The active ingredient usually makes up from 0.5-90% of these powder compositions. The solids ordinarily should be very finely divided. For conversion of the powders to dusts, talc, pyrophyllite, and the like, are customarily used.

Liquid compositions including the active compounds described above can be prepared by admixing the compound with a suitable liquid diluent medium. Typical of the liquid media commonly employed are methanol, benzene, toluene, and the like. The active ingredient usually makes up from about 0.5 to 50% of these liquid compositions. Some of these compositions are designated to be used as such, and others to be extended with large quantities of water.

Compositions in the form of wettable powders or liquids can also include one or more surface active agents, such as wetting, dispersing or emulsifying agents. The surface active agents cause the compositions of wettable powders or liquids to disperse or emulsify easily in water to give aqueous sprays.

The surface active agents employed can be of the anionic, cationic or nonionic type. They include, for example, sodium long-chain carboxylates, alkyl aryl sulfonates, sodium lauryl sulfate, polyethylene oxides, lignin sulfonates and other surface active agents.

When used as a pre-emergent treatment, it is desirable to include a fertilizer, an insecticide, a fungicide or another herbicide.

The amount of compound or composition administered will vary with the particular plant part or plant growth medium which is to be contacted, the general location of application—i.e., sheltered areas such as greenhouses, as compared to exposed areas such as fields —as well as the desired type of control. Generally for both pre- and post-emergent herbicidal control, the compounds of the invention are applied at rates of 0.2 to 60 kg/ha, and the preferred rate is in the range of 0.5 to 40 kg/ha. For plant growth regulating or retarding activity, it is essential to apply the oxime compounds at a concentration not so high as to kill the plants. Therefore, the application rates for plant growth regulating or retarding activity will generally be lower than the rates used for killing the plants. Generally, such rates vary from 0.1 to 5 kg/ha, and preferably from 0.1 to 3 kg/ha.

Herbicidal tests on representative compounds of the invention were made using the following methods.

Pre-Emergent Herbicidal Test

An acetone solution of the test compound was prepared by mixing 375 mg of the compound, 118 mg of a nonionic surfactant and 18 ml of acetone. 10 ml of this solution was added to 40 ml of water to give the test solution.

Seeds of the test vegetation were planted in a pot of soil and the test solution was sprayed uniformly onto the soil surface at a dose of 27.5 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0 to 100 scale was used, 0 representing no phytotoxicity, 100 representing complete kill. The results of these tests appear in Tables I and IA.

Post-Emergent Herbicidal Test

The test compound was formulated in the same manner as described above for the pre-emergent test. This formulation was uniformly sprayed on 2 similar pots of 24-day-old plants (approximately 15 to 25 plants per pot) at a dose of 27.5 microgram/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table I.

EXAMPLE 1

-Preparation of N-Chloroacetyl-2-methyl-6-acetylaniline

A. N-Acetyl 2-methyl-6-acetylaniline (76.1 g) in water (300 ml), ethanol (300 ml), concentrated hydrochloric acid (300 ml) and concentrated sulfuric acid (15 ml) was refluxed for 24 hours. The solution was cooled and concentrated ammonium hydroxide was added to pH 10. The solution was extracted with dichloromethane. The extracts were dried (MgSO$_4$) and stripped. 2-methyl-6-acetylaniline (49.3 g) was obtained as a tan solid.

B. 2-Methyl-6-acetylaniline (25 g) and pyridine (26.5 g) in 1 liter methylene chloride were cooled in an ice acetone bath. A solution of chloroacetyl chloride (37.9 g) in 100 ml methylene chloride was dripped in slowly. The solution was stirred at room temperature for 2 hours, washed with 10% HCl, 10% NaOH, dried (MgSO$_4$) and stripped. Yield: the title product as a white solid, MP 88°–89° C.

Example 2

Preparation of 2,4,5-Trimethyl-2-(3-methyl-2-chloroacetamidophenyl) dioxolane

The product from Example 1 (10.6 g), 2,3-dihydroxy butane (8.5 g) and p-toluene sulfonic acid (1.5 g) in 200 ml benzene were refluxed to 2 hours, removing water with a Dean Stark trap. The solution wash washed with 10% NaOH, dried (MgSO$_4$) and stripped. The product was chromatographed on a silica gel column, eluting with 30% ethyl ether:hexane. Yield: 3.8 g of the title product, mp 55°–57° C.

EXAMPLE 3

Preparation of (3'-methyl-2'-chloroacetamido) acetophenone O-methyloxime

2-Methyl-6-acetylaniline (from Example 1A) was refluxed with methoxyamine hydrochloride in ethanol to yield (3'-methyl-2'-amino) acetophenone O-methyl oxime (I).

Compound I (1.72 g) and 1 g triethylamine in 35 ml methylene chloride were cooled in an ice bath and 1.1 g chloroacetyl chloride was added slowly.

The solution was stirred at room temperature overnight, washed with 10% HCl, 10% NaHCO$_3$, water and dried (MgSO$_4$). The solvent was stripped to yield 1.2 g of the title product, m.p. 119°–120° C.

EXAMPLE 4

Preparation of 2-methyl-6-chlorocarbonyl-nitrobenzene

In this example 2.14 moles of 3-methyl-2-nitrobenzoic acid were refluxed with 6.43 moles (468 ml) of thionyl chloride for three hours and then allowed to stand overnight. The mixture was then again refluxed until the mixture turned a dark brown color. Excess thionyl chloride was removed by evaporation affording 434.4 g of the title product.

EXAMPLE 5

Preparation of 2-methyl-6-methoxycarbonyl-nitrobenzene

In this example a solution containing 1.002 mole of 2-methyl-6-chlorocarbonyl-nitrobenzene in 200 ml of ethyl ether and a small amount of methylene chloride was added to mixture containing 1.5 mole (60.8 ml) of methanol 1.002 mole (139.7 ml) of triethylamine and 200 ml of ethyl ether at about 0° C. The resulting mixture was stirred for one hour and then allowed to stand overnight. The mixture was then filtered and the filtrate washed with dilute aqueous acid and then washed with an aqueous sodium bicarbonate solution. The washed filtrate was dried and evaporated affording 183.3 g of the title product.

Similarly, by using the appropriate alkanol in place of methanol, the corresponding homologs of the title compounds used as starting materials for the corresponding products indicated in Tables A and B can be prepared.

EXAMPLE 6

Preparation of 2-methyl-6-methoxycarbonylaniline

In this example 0.02 mole of 2-methyl-6-methoxycarbonyl-nitrobenzene in 25 ml of acetic acid was added dropwise to a slurry containing 6.5 g of zinc dust suspended in 25 ml of water at 30°-35° C. The resulting exothermic reaction is controlled by maintaining the mixture at about room temperature (about 20°-25° C.) through external cooling. The reaction product mixture was filtered to remove the zinc dust and the filtrate, then washed sequentially with methylene chloride and water, and then extracted with methylene chloride. The extract was washed with an aqueous ammonium hydroxide, then with water and filtered through diatomaceous earth. The filtrate was then dried and evaporated affording 2.7 g of the title product as an oil.

EXAMPLE 7

Preparation of 2-methyl-6-(1-hydroxy-1-methylethyl)-aniline

In this example a solution containing 381.46 g of methyl iodide in 500 ml of ethyl ether was added dropwise to 65.3 g of magnesium submerged in ethyl ether at room temperature and under nitrogen. The mixture was then cooled and then a solution containing 0.67 moles of 2-methyl-6-methoxycarbonylaniline in 500 ml of ethyl ether was dropwise added thereto. The mixture was then refluxed for 2½ hours, then cooled and 750 ml of saturated aqueous ammonium chloride solution carefully added dropwise. Additional ammonium chloride solution was then added and the resulting mixture filtered through diatomaceous earth. The water layer in the filtrate was decanted from the ether layer and washed with ether. The ether washings were combined with the ether layers washed with water, dried and evaporated to dryness affording the title product.

Similarly, by following the same procedure but using the appropriate alkyl or alkenyl iodide and substituted aniline starting materials, corresponding alkyl or alkenyl homologs of the title compounds needed as starting materials for the corresponding products listed in Table B hereinbelow were prepared.

EXAMPLE 8

Preparation of 2-methyl-6-(1-ethoxy-1-methylethyl)-aniline

In this example 0.03 moles of boron trifluoride ethyl etherate was added dropwise to a mixture containing 0.03 moles of 2-methyl-6-(1-hydroxy-1-methylethyl)-aniline in 50 ml of ethanol and 50 ml methylene chloride. The mixture was refluxed for two hours and then allowed to stand for two days. The mixture was then poured into about 700 ml of saturated aqueous sodium bicarbonate solution stirred and extracted with methylene chloride. The extract was filtered through diatomaceous earth, dried and evaporated affording 5.4 g of the title product as an oil.

Similarly, by following the same procedure using the appropriate alkanol or alkenol starting material and boron trifluoride etherate, the corresponding intermediates for the products listed in Table B hereinbelow were prepared.

EXAMPLE 9

Preparation of—Preparation of 2-methyl-6-(1-ethoxy-1-methylethyl)-N-chloroacetylaniline In this example 1.45 g (1.03 ml) of chloroacetyl chloride was added dropwise to a solution containing 1.44 g (2 ml) of triethylamine and 0.0129 mole of 2-methyl-6-(1-ethoxy-1-methylethyl)aniline in methylene chloride at about but below 20° C. The mixture was then refluxed and then allowed to stand overnight at room temperature. Another 0.51 ml of chloroacetyl chloride and 1 ml of triethylamine was then added dropwise. The mixture was then again refluxed and allowed to stand overnight at room temperature. The mixture was then washed with saturated aqueous sodium bicarbonate, dried and evaporated affording the title compound as a brown oil.

EXAMPLE 10

Preparation of 2-methyl-6(1'-methylprop-1-enyl)-N-chloroacetylaniline

In this example a mixture of 0.0089 mole of 2'-methyl-6'-(1-hydroxy-1-methylpropyl)-aniline was saturated with gaseous hydrogen chloride and then refluxed for one hour. The mixture was then poured into aqueous 10% (wt.) sodium hydroxide. The organic phase was separated washed with aqueous 10% (wt.) sodium hydroxide and extracted with methylene chloride. The extract was then dried and evaporated affording a mixture of the cis and trans isomers of 2'-methyl-6'-(1-methylprop-1-enyl)-aniline as an oil.

0.007 mole of chloroacetyl chloride was added dropwise to a mixture of 0.007 moles of 2-methyl-6-(1-methylprop-1-enyl)-aniline and 0.008 moles (1.15 ml) of triethylamine in methylene chloride at about but below 20° C. The mixture was then refluxed and then allowed to stand overnight at room temperature. The mixture was then again refluxed and allowed to stand for two days (over the weekend) at room temperature. Thin layer chromatographic (plate) analysis showed the presence of a small amount of starting material. An additional 0.55 ml of triethylamine and 0.3 ml of chloroacetyl chloride was added and the mixture again refluxed and allowed to stand overnight at room temperature.

The mixture was then washed with aqueous sodium bicarbonate, dried and evaporated affording 1.7 g of the title compound as a slightly crystallized oil (m.p. 71°-74° C.).

EXAMPLE 11

Preparation of 2-Methyl-6-(1-methyl-1-methoxyethyl)-N-chloroacetylaniline

In this example 234.93 g (9.66 moles) of magnesium was placed under nitrogen and then mixed with 583 ml of ethyl ether at room temperature. A small amount of methyl iodide was then added with gentle stirring followed by the addition of another 468 ml of ethyl ether. A methyl iodide solution containing 1,371.72 g (9.66 moles) of methyl iodide in 468 ml of ethyl ether was slowly added at reflux over a 2¼-2½-hour period. (During this period the mixture was diluted with another 583 ml of ethyl ether to reduce the reaction rate.) The mixture was cooled to room temperature and then a solution containing 433.9 g of 2-methyl-6-acetylaniline dissolved in 698 ml of ethyl ether was slowly added over 1¼-1½ hours. During this addition the temperature of the mixture was maintained at about or below 25° C. The mixture was then stirred at room temperature for another hour. Three liters of methylene chloride was then added at about 25° C. and the reaction was then quenched by the addition of solid ammonium chloride and water. The mixture was then allowed to stand overnight (about 15 hours). The ether phase of the mixture was then separated and filtered. The water phase was mixed with three liters of methylene chloride filtered. The methylene chloride filtrate and the ethyl ether filtrate were each evaporated affording 2-methyl-6-(1-methyl-1-hydroxyethyl)-aniline.

231.0 g (1.4 mols) of the above product was dissolved in 5.775 liters of methanol. This solution was then saturated with hydrogen chloride gas and refluxed. Upon completion of the reaction, the solution was evaporated affording the hydrogen chloride salt of the methyl ether. This salt was then dissolved in 1.4 liters of methylene chloride and then treated with aqueous 10% wt. sodium hydroxide until about neutral. The methylene chloride layer was then separated, dried over magnesium sulfate and evaporated affording 240 g of 2-methyl-6-(1-methyl-1-methoxyethyl)-aniline. A second batch of this product was made in the same manner.

216.46 g (2.74 mols) of pyridine was slowly added to a solution containing 467.5 g (2.61 mols) of 2-methyl-6-(1-methyl-1-methoxyethyl)-aniline in 2.74 liters of methylene chloride at room temperature (about 18°-25° C.). 309.62 g (2.74 mols) of chloroacetyl chloride was added dropwise over a 20-minute period. The temperature of the mixture was maintained at about, or less than, 25° C. during this addition. The mixture was then stirred at about 18° C. for about 1 hour and then mixed with two liters of water. The methylene chloride phase was then separated treated with aqueous 5 wt. % hydrochloric acid until slightly acidic and then washed with water and dried over magnesium sulfate. The mixture was then evaporated to dryness affording a brownish solid which was then washed with a 10% isopropanol:90% hexane mixture affording 484 g of the title compound.

Similarly, by following the same procedure but using 2-methyl-6-acetyl-N-methylaniline as the starting material, the corresponding N-methyl homolog of the title compound can be prepared.

TABLE A

Compounds of the Formula

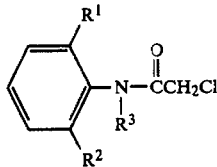

| No. | $R^1$ | $R^3$ | $R^2$ | m.p. °C. | C Calculated | C Found | H Calculated | H Found | N Calculated | N Found |
|---|---|---|---|---|---|---|---|---|---|---|
| 1 | $CH_3$ | H | $-\underset{CH_3}{C}=NOC_2H_5$ | 86-87 | 13.2ᵃ | 16.1ᵃ | | | | |
| 2 | $CH_3$ | H | $-\underset{CH_3}{C}(OCH_3)_2$ | oil | 57.45 | 59.92 | 6.68 | 5.47 | 5.16 | 5.27 |
| 3 | $CH_3$ | H | $-\underset{CH_3}{C}=NOCH_3$ | 119-120 | 56.58 | 56.85 | 5.94 | 5.16 | 5.0 | 5.24 |
| 4 | $CH(CH_3)_2$ | H | $-\underset{CH_3}{C}=NOCH_3$ | 108-110 | 59.46 | 50.62 | 6.77 | 5.82 | 9.91 | 9.53 |
| 5 | $CH_3$ | $C_2H_5$ | $-\underset{CH_3}{C}(OCH_3)_2$ | 61-64 | 60.09 | 59.21 | 7.40 | 7.33 | 4.67 | 4.48 |

TABLE A-continued

Compounds of the Formula

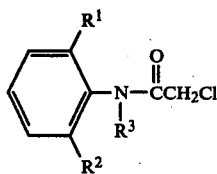

| No. | R¹ | R³ | R² | m.p. °C. | C Calculated | C Found | H Calculated | H Found | N Calculated | N Found |
|---|---|---|---|---|---|---|---|---|---|---|
| 6 | $CH_3$ | $C_2H_5$ | $-C(OCH_3)=CH_2$ | oil | 62.80 | 61.44 | 6.78 | 6.96 | 5.23 | 4.87 |
| 7 | $CH_3$ | H | $-C(=O)-C_2H_5$ | 75–77 | 60.13 | 59.76 | 5.89 | 6.05 | 5.84 | 5.69 |
| 8 | $CH_3$ | $C_2H_5$ | $-C(=O)-CH_3$ | oil | 61.53 | 59.07 | 6.36 | 6.08 | 5.52 | 5.12 |
| 9 | $CH_3$ | H | $-CH(OH)CH_3$ | 77–79 | 58.02 | 55.7 | 6.20 | 6.14 | 6.15 | 6.0 |
| 10 | $C_2H_5$ | H | $-CH(OH)CH_3$ | 113–114 | 59.62 | 58.89 | 6.67 | 6.75 | 5.80 | 6.0 |
| 11 | $CH_3$ | H | $-C(=O)CH_3$ | 88–89 | 58.54 | 54.53 | 5.36 | 4.95 | 6.21 | 5.7 |
| 12 | $CH(CH_3)_2$ | H | $-C(=O)CH_3$ | 118–120 | 61.53 | 56.71 | 6.36 | 5.59 | 5.52 | 4.29 |
| 13 | $CH_3$ | H | $-C(CH_3)=CH_2$ | oil (71–74) | 65.7 | 64.5 | 6.8 | 6.7 | 5.9 | 5.2 |
| 13a | $CH_3$ | $-C_2H_5$ | $-C(OCH_3)=CH_2$ | oil | 62.80 | 61.44 | 6.78 | 6.96 | 5.23 | 4.87 |
| C-1 | $CH_3$ | $-CH_2OCH_3$ | $-CH_2OCH_3$ | oil | 57.5 | 59.6 | 6.7 | 6.9 | 5.2 | 5.6 |

*a* = chlorine

TABLE B

Compounds of the Formula

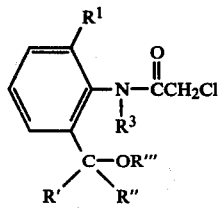

| No. | R¹ | R³ | R' | R'' | R''' | m.p. °C. | C Calc. | C Found | H Calc. | H Found | N Calc. | N Found |
|---|---|---|---|---|---|---|---|---|---|---|---|---|
| 14 | $CH_3$ | H | $CH_3$ | $CH_3$ | $CH_3$ | oil | 61.1 | 59 | 7.1 | 7 | 5.5 | 2.2 |
| 15 | $CH_3$ | H | $CH_3$ | $CH_3$ | $C_2H_5$ | oil | 62.3 | 62.3 | 7.5 | 7.6 | 5.2 | 4.9 |
| 16 | $CH_3$ | H | $CH_3$ | $CH_3$ | $C_3H_7$ | oil | 63.5 | 62.6 | 7.8 | 8.2 | 4.9 | 4.55 |
| 17 | $CH_3$ | H | $CH_3$ | $CH_3$ | $CH_2CH=CH_2$ | oil | 63.9 | 63.5 | 7.15 | 7.0 | 5.0 | 5.1 |
| 18 | $CH_3$ | H | $CH_3$ | $n-C_4H_9$ | $CH_3$ | oil | 64.5 | 61.5 | 8.1 | 7.8 | 4.7 | 4.1 |
| 19 | $CH_3$ | H | $C_2H_5$ | $C_2H_5$ | $CH_3$ | oil | 63.5 | 64.3 | 7.8 | 8.2 | 4.9 | 4.9 |
| 20 | $CH_3$ | H | $CH_3$ | $CH(CH_3)_2$ | $CH_3$ | oil | 63.5 | 60.0 | 7.8 | 6.9 | 4.9 | 4.2 |

TABLE B-continued

Compounds of the Formula

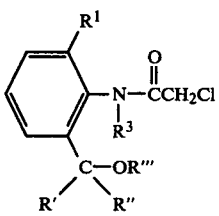

| No. | R¹ | R³ | R' | R'' | R''' | m.p. °C. | C Calc. | C Found | H Calc. | H Found | N Calc. | N Found |
|---|---|---|---|---|---|---|---|---|---|---|---|---|
| 21 | CH₃ | CH₃ | CH₃ | CH₃ | CH₃ | oil | 62.3 | 62.7 | 7.5 | 7.5 | 5.2 | 4.9 |
| 22 | CH₃ | H | H | CH₃ | CH₃ | solid | 59.6 | 60.2 | 6.7 | 6.8 | 5.8 | 5.9 |
| 23 | CH₃ | H | H | H | CH₃ | — | 58.0 | 57.4 | 6.2 | 6.3 | 6.2 | 6.4 |
| 24 | CH₃ | H | CH₃ | CH₃ | —CH₂CH=CH₂ | oil | 63.9 | 63.45 | 7.15 | 7.0 | 5.0 | 5.1 |

TABLE I
HERBICIDAL ACTIVITY

| | Pre/Post | | | % Control | | |
|---|---|---|---|---|---|---|
| No. | L | M | P | C | W | O |
| 1 | 65/60 | 60/60 | 75/20 | 97/60 | 100/60 | 99/15 |
| 2 | 55/0 | 55/0 | 60/0 | 100/20 | 100/45 | 98/20 |
| 3 | 0/0 | 0/0 | 0/0 | 90/0 | 90/0 | 55/0 |
| 4 | 0/0 | 0/0 | 0/0 | 90/0 | 90/0 | 50/0 |
| 5 | 10/0 | 0/0 | 0/0 | 95/0 | 100/0 | 70/0 |
| 6 | 50/0 | 78/0 | 95/0 | 100/65 | 100/85 | 98/20 |
| 7 | 0/0 | 30/0 | 0/0 | 92/0 | 95/30 | 90/10 |
| 8 | 45/0 | 82/0 | 85/0 | 100/55 | 100/85 | 95/20 |
| 9 | 0/0 | 0/0 | 0/0 | 100/0 | 90/0 | 15/0 |
| 10 | 40/0 | 30/0 | 60/0 | 95/0 | 100/60 | 15/0 |
| 11 | 0/0 | 0/0 | 0/0 | 90/0 | 95/0 | 0/0 |
| 12 | 0/30 | 0/20 | 0/25 | 95/15 | 97/15 | 30/0 |

L = Lambsquarter (Chenopodium album)
M = Mustard (Brassica arvensis)
P = Pigweed (Amaranthus retroflexus)
C = Crabgrass (Digitaria sanguinalis)
W = Watergrass (Echinochola crusgalli)
O = Wild Oats (Avenua fatua)

TABLE IA
PRE-EMERGENCE HERBICIDAL ACTIVITY

| | Pre-Emergence | | | % Control | | | |
|---|---|---|---|---|---|---|---|
| No. | L | M | P | C | W | O | S | R |
| 13 | 100 | 60 | 60 | 100 | 100 | 88 | 60 | 60 |
| 13a | 0 | 0 | 0 | 90 | 95 | 40 | 0 | 50 |
| 14 | 100 | 85 | 100 | 100 | 100 | 100 | 80 | 98 |

TABLE IA-continued
PRE-EMERGENCE HERBICIDAL ACTIVITY

| | Pre-Emergence | | | % Control | | | |
|---|---|---|---|---|---|---|---|
| No. | L | M | P | C | W | O | S | R |
| 15 | 70 | 60 | 70 | 100 | 100 | 99 | 63 | 100 |
| 16 | 75 | 65 | 70 | 100 | 100 | 88 | 15 | 100 |
| 17 | 85 | 65 | 75 | 100 | 100 | 98 | 50 | 100 |
| 18 | 65 | 60 | 80 | 100 | 100 | 93 | 40 | 100 |
| 19 | 100 | 98 | 100 | 100 | 100 | 93 | 85 | 100 |
| 20 | 95 | 72 | 88 | 100 | 100 | 95 | 80 | 100 |
| 21 | 99 | 73 | 85 | 100 | 100 | 93 | 83 | 100 |
| 22 | 93 | 80 | 83 | 98 | 100 | 80 | 0 | 80 |
| 23 | 25 | 10 | 0 | 100 | 100 | 45 | 0 | 45 |
| 24 | 85 | 65 | 75 | 100 | 100 | 98 | 50 | 100 |

L = Lambsquarter (Chenopodium album)
M = Mustard (Brassica arvensis)
P = Pigweed (Amaranthus retroflexus)
C = Crabgrass (Digitaria sanguinalis)
W = Watergrass (Echinochola crusgalli)
O = Wild Oats (Avenua fatua)
S = Soy Bean
R = Ryegrass As can be seen from the above table, the compounds listed in this table exhibit pre-emergence herbicidal activity and especially so the compounds identified as 14 (i.e. 2'-methyl-6'-(1-methyl-1-methoxyethyl)-N-chloroacetylaniline); 19 (i.e. 2'-methyl-6'-(1-ethyl-1-methoxypropyl)-N-chloroacetylaniline) and 21 (i.e. 2'-methyl-6'-(1-methyl-1-methoxyethyl)-N-methyl-N-chloroacetylaniline, with respect to herbicidal activity against grasses.

TABLE II
Pre-Emergence Herbicidal Activity
Low Dosage Tests

| | | Grasses % Phytotoxicity | | | | | | | |
|---|---|---|---|---|---|---|---|---|---|
| Compound # | Dosage γ/cm²* | Crab Grass | Water Grass | Wild Oats | Cheat Grass | Johnson Grass | Rye Grass | Switch Grass | Yellow Foxtail | Yellow Nutsedge |
| 14 | 4.4 | 100 | 100 | 100 | 100 | 99 | 99 | 100 | 100 | 100 |
| 21 | 4.4 | 100 | 100 | 95 | 97 | 98 | 100 | 100 | 100 | 100 |
| 19 | 4.4 | 100 | 100 | 90 | 100 | 100 | 100 | 100 | 100 | 97 |
| 15 | 4.4 | 93 | 95 | 53 | 92 | 95 | 100 | 18 | 100 | 17 |
| 16 | 4.4 | 60 | 92 | 0 | — | — | — | — | — | 47 |
| 17 | 4.4 | 80 | 100 | 47 | — | — | — | — | — | 30 |
| 18 | 4.4 | 38 | 90 | 13 | — | — | — | — | — | — |
| 22 | 4.4 | 63 | 92 | 53 | — | — | — | — | — | 17 |
| 23 | 4.4 | 37 | 73 | 7 | — | — | — | — | — | 47 |
| 24 | 4.4 | 80 | 100 | 47 | — | — | — | — | — | 30 |
| 2 | 4.4 | 15 | 3 | 0 | — | — | — | — | 72 | 23 |
| 13a | 4.4 | 82 | 85 | 0 | — | — | — | — | 95 | 0 |

*γ/cm² = micrograms per square centimeter

TABLE IIa
Pre-Emergence Herbicidal Activity
Low Dosage Tests

| Compound # | Dosage γ/cm²* | Crab Grass | Water Grass | Wild Oats | Cheat Grass | Johnson Grass | Rye Grass | Switch Grass | Yellow Foxtail | Yellow Nutsedge |
|---|---|---|---|---|---|---|---|---|---|---|
| 14 | 1.8 | 100 | 99 | 95 | 98 | 92 | 85 | 99 | 100 | 93 |
| 21 | 1.8 | 77 | 100 | 53 | 97 | 96 | 100 | 100 | 100 | 97 |
| 19 | 1.8 | 100 | 100 | 70 | 100 | 98 | 99 | 100 | 100 | 62 |
| 15 | 1.8 | 80 | 88 | 0 | 65 | 68 | 85 | 87 | 99 | 97 |
| 16 | 1.8 | 20 | 20 | 0 | — | — | — | — | — | 43 |
| 17 | 1.8 | 0 | 88 | 10 | — | — | — | — | — | 60 |
| 18 | 1.8 | 38 | 33 | 0 | — | — | — | — | — | 38 |
| 22 | 1.8 | 13 | 48 | 7 | — | — | — | — | — | 37 |
| 23 | 1.8 | 0 | 40 | 0 | — | — | — | — | — | 0 |
| 24 | 1.8 | 0 | 88 | 10 | — | — | — | — | — | 60 |
| 2 | 1.8 | 0 | 0 | 0 | — | — | — | — | 20 | 0 |
| 13a | 1.8 | 45 | 48 | 0 | — | — | — | — | 58 | 0 |

*γ/cm² = micrograms per square centimeter

TABLE IIb
Pre-Emergence Herbicidal Activity
Low Dosage Tests

| Compound # | Dosage γ/cm²* | Crab Grass | Water Grass | Wild Oats | Cheat Grass | Johnson Grass | Rye Grass | Switch Grass | Yellow Foxtail | Yellow Nutsedge |
|---|---|---|---|---|---|---|---|---|---|---|
| 14 | 0.7 | 100 | 98 | 37 | 68 | 67 | 73 | 73 | 100 | 52 |
| 21 | 0.7 | 65 | 92 | 10 | 37 | 58 | 74 | 82 | 93 | 75 |
| 19 | 0.7 | 82 | 100 | 40 | 99 | 67 | 95 | 90 | 100 | 62 |
| 15 | 0.7 | 7 | 37 | 0 | 7 | 10 | 42 | 28 | 95 | 68 |
| 16 | 0.7 | 0 | 0 | 0 | — | — | — | — | — | 0 |
| 17 | 0.7 | 0 | 53 | 0 | — | — | — | — | — | 42 |
| 18 | 0.7 | 0 | 0 | 00 | — | — | — | — | — | 0 |
| 22 | 0.7 | 0 | 7 | 0 | — | — | — | — | — | 0 |
| 23 | 0.7 | 0 | 0 | 0 | — | — | — | — | — | 0 |
| 24 | 0.7 | 0 | 53 | 0 | — | — | — | — | — | 42 |
| 2 | 0.7 | 0 | 0 | 0 | — | — | — | — | — | 0 |
| 13a | 0.7 | 0 | 0 | 0 | — | — | — | — | 0 | 0 |

*γ/cm² = micrograms per square centimeter

TABLE IIc
Pre-Emergence Herbicidal Activity
Low Dosage Tests

| Compound # | Dosage γ/cm²* | Crab Grass | Water Grass | Wild Oats | Cheat Grass | Johnson Grass | Rye Grass | Switch Grass | Yellow Foxtail | Yellow Nutsedge |
|---|---|---|---|---|---|---|---|---|---|---|
| 14 | 0.28 | 95 | 97 | 0 | 7 | 12 | 53 | 8 | 99 | 37 |
| 21 | 0.28 | 33 | 65 | 0 | 42 | 40 | 82 | 38 | 100 | 43 |
| 19 | 0.28 | 8 | 85 | 0 | 13 | 32 | 7 | 20 | 72 | 22 |
| 15 | 0.28 | 0 | 0 | 0 | 0 | 2 | 7 | 0 | 87 | 32 |
| 16 | 0.28 | 0 | 0 | 0 | — | — | — | — | — | 0 |
| 17 | 0.28 | 0 | 0 | 0 | — | — | — | — | — | 0 |
| 18 | 0.28 | 0 | 0 | 0 | — | — | — | — | — | 0 |
| 22 | 0.28 | 0 | 0 | 0 | — | — | — | — | — | 0 |
| 23 | 0.28 | 0 | 0 | 0 | — | — | — | — | — | 0 |
| 24 | 0.28 | 0 | 0 | 0 | — | — | — | — | — | 0 |
| 2 | 0.70 | 0 | 0 | 0 | — | — | — | — | — | 0 |
| 13a | 0.70 | 0 | 0 | 0 | — | — | — | — | — | 0 |

*γ/cm² = micrograms per square centimeter

TABLE III
Pre-Emergence Herbicidal Activity
Low Dosage Test
Broad-Leaf Crops
% Phytotoxicity

| Compound # | Dosage γ/cm²* | Soybean | Alfalfa | Cotton | Peanuts | Peas | Sugar Beets | Tomatoes |
|---|---|---|---|---|---|---|---|---|
| 14 | 4.4 | 63 | 100 | 60 | 53 | 100 | 100 | 100 |
| 14 | 1.8 | 43 | 98 | 48 | 27 | 85 | 88 | 87 |
| 14 | 0.7 | 5 | 94 | 15 | 7 | 42 | 77 | 58 |
| 14 | 0.28 | 0 | 62 | 10 | 0 | 77 | 23 | 0 |

TABLE III-continued

| | | Pre-Emergence Herbicidal Activity Low Dosage Test | | | | | | |
|---|---|---|---|---|---|---|---|---|
| | | Broad-Leaf Crops % Phytotoxicity | | | | | | |
| Compound # | Dosage $\gamma/cm^{2*}$ | Soybean | Alfalfa | Cotton | Peanuts | Peas | Sugar Beets | Tomatoes |
| 21 | 4.4 | 23 | 89 | 23 | 20 | 67 | 96 | 97 |
| 21 | 1.8 | 3 | 77 | 13 | 8 | 22 | 90 | 75 |
| 21 | 0.7 | 0 | 22 | 0 | 7 | 18 | 28 | 0 |
| 21 | 0.28 | 0 | 15 | 0 | 0 | 15 | 7 | 0 |
| 19 | 4.4 | 70 | 94 | 40 | 10 | 82 | 98 | 75 |
| 19 | 1.8 | 32 | 68 | 15 | 0 | 52 | 78 | 35 |
| 19 | 0.7 | 7 | 73 | 0 | 0 | 5 | 68 | 3 |
| 19 | 0.28 | 0 | 50 | 0 | 0 | 0 | 8 | 0 |

The results shown in Tables II, IIa, IIb, and IIc show that compounds 14, 19, and 21, representing the subgenus of Formula I' have very substantially superior pre-emergence herbicide activity against grasses to even very closely related compounds. The results shown in Table III show that compounds 14, 19, and 21 can be safely applied at grass herbicide effective dosages with respect to cotton, peanut and soybean crops. (A phytotoxicity of less than about 25% is generally considered safe as the crop as a whole will generally grow out of this amount of phytotoxicity.)

Obviously, many modifications and variations of the invention, described hereinabove and below, can be made without departing from the essence and scope thereof.

What is claimed is:

1. A compound having the formula:

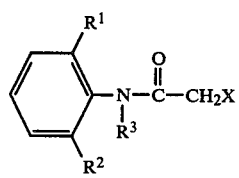

wherein $R^1$ is methyl;
$R^2$ is 1,1-dimethoxyethyl;
$R^3$ is hydrogen, methyl or ethyl; and X is halogen.

2. The compound of claim 1 wherein $R^3$ is hydrogen, or ethyl and X is chloro.

3. The compound of claim 1 wherein X is chloro.

4. A compound having the formula:

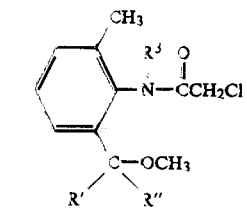

wherein $R^3$ is hydrogen or methyl and R' and R" are independently methyl or ethyl.

5. The compound of claim 4 wherein R' and R" are each methyl.

6. The compound claim 5 wherein $R^3$ is hydrogen.

7. The compound of claim 5 wherein $R^3$ is methyl.

8. The compound of claim 4 wherein one of R' or R" is methyl and the other is ethyl.

9. The compound of claim 8 wherein $R^3$ is hydrogen.

10. The compound of claim 4 wherein R' and R" are each ethyl.

11. The compound of claim 10 wherein $R^3$ is hydrogen.

12. The compound of claim 10 wherein $R^3$ is methyl.

13. An herbicidal composition comprising a biologically inert carrier and an herbicidally effective amount of the compound of claim 1.

14. An herbicidal composition comprising a biologically inert carrier and an herbicidally effective amount of the compound of claim 4.

15. An herbicidal composition comprising a biologically inert carrier and an herbicidally effective amount of the compound of claim 6.

16. A method for preventing or retarding the growth of grasses which comprises applying to its growth environment an herbicidally effective amount of the compound of claim 1.

17. A method for preventing or retarding the growth of grasses which comprises applying to its growth environment an herbicidally effective amount of the compound of claim 4.

18. A method for preventing or retarding the growth of grasses which comprises applying to its growth environment an herbicidally effective amount of the compound of claim 6.